(12) United States Patent
Raphael

(10) Patent No.: US 8,409,096 B2
(45) Date of Patent: Apr. 2, 2013

(54) BREATHING CIRCUIT WITH EMBEDDED ACOUSTIC REFLECTOMETER

(75) Inventor: David T. Raphael, Valley Village, CA (US)

(73) Assignee: University of Southern California, Los Angeles, CA (US)

( * ) Notice: Subject to any disclaimer, the term of this patent is extended or adjusted under 35 U.S.C. 154(b) by 562 days.

(21) Appl. No.: 12/469,492

(22) Filed: May 20, 2009

(65) Prior Publication Data
US 2009/0318805 A1 Dec. 24, 2009

Related U.S. Application Data

(60) Provisional application No. 61/074,290, filed on Jun. 20, 2008.

(51) Int. Cl.
*A61B 8/00* (2006.01)
*A62B 9/02* (2006.01)
(52) U.S. Cl. .................................. 600/439; 128/207.16
(58) Field of Classification Search .................. None
See application file for complete search history.

(56) References Cited

U.S. PATENT DOCUMENTS

| 4,821,736 | A | * | 4/1989 | Watson | ........................ 600/532 |
| 5,303,698 | A |  | 4/1994 | Tobia et al. | |
| 6,644,311 | B1 | * | 11/2003 | Truitt et al. | ............. 128/204.22 |
| 2003/0034035 | A1 |  | 2/2003 | Raphael | |
| 2007/0286024 | A1 |  | 12/2007 | Raphael | |

FOREIGN PATENT DOCUMENTS
EP 1352670 A1 10/2003

OTHER PUBLICATIONS

Pennant, JH. Comparison of the Endotracheal Tube and Laryngeal Mask ~ in Airway Management by Paramedical Personnel. Anesthesia and Analgesis 1992, vol. 74, pp. 531-534.*
Raphael DT. Acoustic Reflectometry Profiles of Endotracheal and Esophageal Intubation. Anesthesiology 2000, vol. 92, pp. 1293-1299.*
Klarskov et al. Pressure reflectometry: in vitro recordings with a new technique for simultaneous measurement of cross-sectional area and pressure in a collapsible tube. Physiological Measurement 2005, vol. 26, pp. 269-280.*
Dorsch, J. et al. Understanding Anesthesia Equipment. (4th Edition), Lippincott Williams and Wilkins, Baltimore, MD 1999, pp. 183-269.
International Search Report for PCT Application Serial No. PCT/US09/047951, mailed on Aug. 7, 2009.

* cited by examiner

*Primary Examiner* — Louise Humphrey
(74) *Attorney, Agent, or Firm* — McDermott Will & Emery LLP

(57) ABSTRACT

An instrument may continuously monitoring acoustic reflections from within and/or beyond an intubation tube positioned within the mouth of a patient while the patient is breathing. The instrument may include an acoustic reflectometer configured to detect the acoustic reflections. An acoustic flow channel may contain the acoustic reflectometer within it. The acoustic flow channel may be configured to acoustically couple the acoustic reflectometer to an end of the intubation tube, but to substantially block the free flow of expiratory gas from the end of the intubation tube through the acoustic flow channel. A gas flow channel may be separate from the acoustic flow channel and may be configured to allow the free flow of expiratory gas from the end of the intubation tube through the gas flow channel.

15 Claims, 6 Drawing Sheets

BREATHING CIRCUIT WITH EMBEDDED ACOUSTIC REFLECTOMETER

CROSS-REFERENCE TO RELATED APPLICATION(S)

This application is based upon and claims priority to U.S. Provisional Patent Application No. 61/074,290, entitled "Modified Breathing Circuit For Acoustic Reflectometry," filed Jun. 20, 2008. The entire content of this application is incorporated herein by reference.

BACKGROUND

1. Technical Field

This disclosure relates to breathing circuits and to acoustic reflectometers.

2. Description of Related Art

Acoustic reflectometers are used to detect obstructions in intubation tubes and in cavities beyond them. Breathing circuits are used to assist a patient with breathing.

Although related, an acoustic reflectometer is not usually used at the same time as a breathing circuit because the components of the acoustic reflectometer may be adversely affected by the humidity, pressure and/or temperature of expiratory gas in the breathing circuit. Instead, acoustic reflectometers are typically attached to an intubation tube only temporarily while measurements are made, detached while normal breathing takes place, and attached and detached again as needed for further measurements. This can increase needed labor and delay notice of a sudden obstruction.

SUMMARY

An instrument may continuously monitor acoustic reflections from within and/or beyond an intubation tube positioned within the mouth of a patient while the patient is breathing. The instrument may include an acoustic reflectometer configured to detect the acoustic reflections. An acoustic flow channel may contain the acoustic reflectometer within it. The acoustic flow channel may be configured to acoustically couple the acoustic reflectometer to an end of the intubation tube, but to substantially block the free flow of expiratory gas from the end of the intubation tube through the acoustic flow channel. A gas flow channel may be separate from the acoustic flow channel and may be configured to allow the free flow of expiratory gas from the end of the intubation tube through the gas flow channel.

The intubation tube and the acoustic flow channel may each share a substantially common central axis. The end of the intubation tube and the acoustic flow channel may each have a substantially cylindrical cross-section of approximately the same diameter.

The instrument may include a gas valve configured when in a closed position to block expiratory gas from flowing from the end of the intubation tube into the acoustic flow channel.

The gas valve may have an open position at which the valve does not cause a substantial disruption in acoustic energy traveling from the acoustic reflectometer within the acoustic gas channel into the end of the intubation tube.

The gas valve may be located at an end of the acoustic flow channel which is closest to the end of the intubation tube and the instrument may include a second gas valve located at the other end of the acoustic flow channel.

The instrument may include a gas valve controller configured to control the gas valves.

The instrument may include a gas flow sensor configured to sense the flow of gas through the end of the intubation tube. The gas valve controller may be configured to cause the gas valve to be in the closed position when the gas flow sensor detects the flow of expiratory gas from the end of the intubation tube.

The gas valve controller may be configured to cause the gas valve to be in the closed position when the gas flow sensor detects the flow of inspiratory gas through the end of the intubation tube. The gas valve controller may be configured to cause the gas valve to momentarily move to the open position between the end of the flow of expiratory gas from the end of the intubation tube and the beginning of the flow of inspiratory gas into the end of the intubation tube.

The instrument may include a second gas flow channel that is separate from the acoustic flow channel and the other gas flow channel and that is configured to allow the free flow of inspiratory gas through the second gas flow channel and into the end of the intubation tube.

The instrument may include a gas valve configured when in a closed position to allow the free flow of inspiratory gas from the gas flow channel into the end of the intubation tube. The gas valve may be configured when in an open position to allow the free flow of inspiratory gas to flow through the acoustic flow channel into the end of the intubation tube and to block inspiratory gas from flowing though the gas flow channel into the end of the intubation tube.

The gas flow channel may include a humidifier configured to humidify gas which passes through the gas flow channel.

The acoustic reflectometer may include components and the instrument may include a heater configured to heat one or more of the components. A hydrophobic substance may cover one or more of the components.

The instrument may include a coupling configured to detachably couple the instrument to the end of the intubation tube.

The instrument may include the intubation tube. The intubation tube may be an endotracheal tube, a laryngeal mask airway tube, or any other airway device with a central passageway for gas flow.

The acoustic flow channel and the gas flow channel may run parallel to one another within a single tube. The central axis of the single tube may be substantially co-aligned with the central axis of the acoustic flow channel and the central axis of the gas flow channel.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings disclose illustrative embodiments. They do not set forth all embodiments. Other embodiments may be used in addition or instead. Details that may be apparent or unnecessary may be omitted to save space or for more effective illustration. Conversely, some embodiments may be practiced without all of the details that are disclosed. When the same numeral appears in different drawings, it is intended to refer to the same or like components or steps.

DETAILED DESCRIPTION OF ILLUSTRATIVE EMBODIMENTS

Illustrative embodiments are now discussed. Other embodiments may be used in addition or instead. Details that may be apparent or unnecessary may be omitted to save space or for a more effective presentation. Conversely, some embodiments may be practiced without all of the details that are disclosed.

Figure 1A:
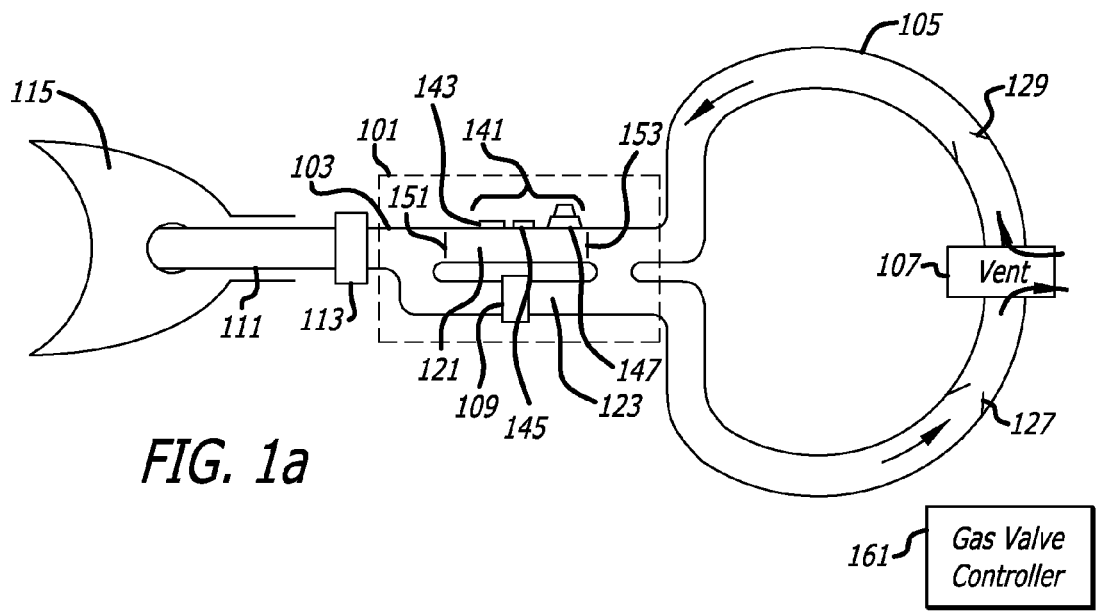
FIG. 1(a) illustrates an instrument for continuously monitoring acoustic reflections from within and/or beyond an intubation tube positioned within the mouth of a patient while the patient is breathing. The instrument is in an inactive state.
Figure 1B:
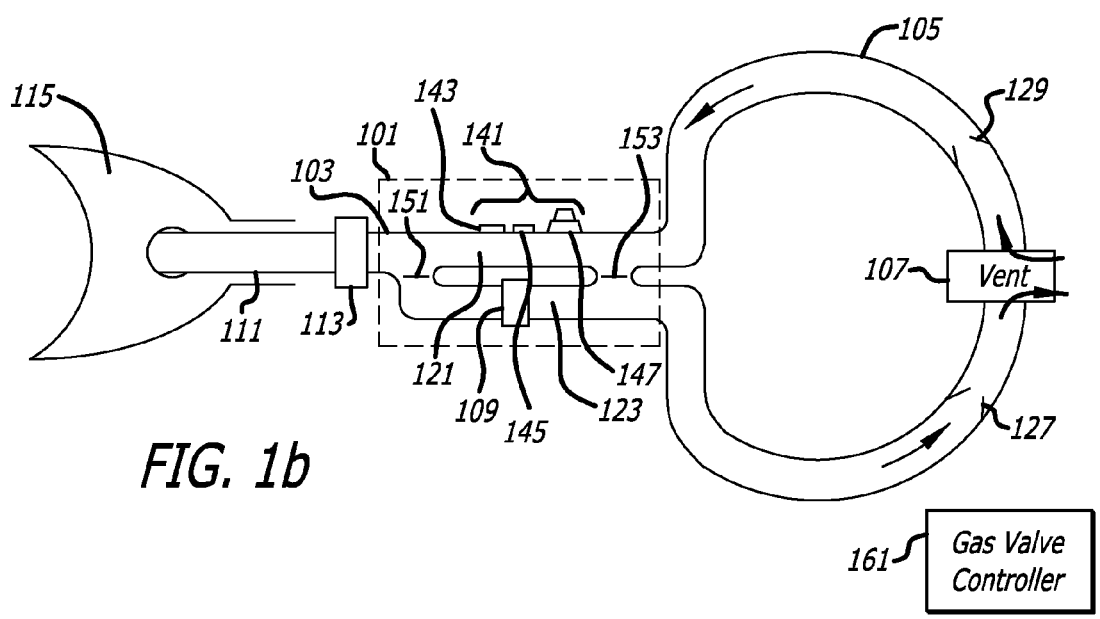
FIG. 1(b) illustrates the instrument in FIG. 1(a) in an active state.

FIG. 1(a) illustrates an instrument for continuously monitoring acoustic reflections from within and/or beyond an intubation tube positioned within the mouth of a patient while the patient is breathing. The instrument is in a inactive state. FIG. 1(b) illustrates the instrument in FIG. 1(a) in an active state.

As illustrated in FIGS. 1(a) and (b), the instrument may include a valve and channel arrangement 101, a neck 103, a circular channel 105, a vent 107, and a humidifier 109. The neck 103 may be detachably coupled to an intubation tube 111 using a detachable coupling 113.

The intubation tube 111 may be positioned within a mouth of a patient while the patient is breathing. The intubation tube may be an endotracheal tube which extends into a lung 115 of the patient. The intubation tube 111 may instead be a laryngeal mask airway tube which does not extend into the lung 115. The intubation tube 111 may instead be of a different type and/or for a different purpose, such as any other airway device with a central passageway for gas flow.

The valve and channel arrangement 101 may include an acoustic flow channel 121 and a gas flow channel 123.

The circular channel 105 may include one or more one-way gas valves, such as a one-way gas valve 127 and a one-way gas valve 129. The circular channel 105 may include a vent 107.

Although denominated as merely a "vent" herein, the vent 107 may be part of an anesthesia system or ICU ventilator system that connects to the breathing circuit through connections to the inspiratory and expiratory limbs of the breathing circuit. Such a system may contain an inlet for fresh gas flow, a reservoir bag, a scavenging system, a $CO_2$ absorption canister, a ventilator/manual bag selector switch (to switch between mechanical ventilation versus spontaneous or manual ventilation), and/or a mechanical ventilator. An example, one such system may be found in Jerry A. Dorsch and Susan E. Dorsch, "Understanding Anesthesia Equipment" (4th Edition), Lippincott Williams and Wilkins, Baltimore, Md. 1999, pages 183-269, the entire contents of which are incorporated herein by reference.

The one-way gas valve 127 may be configured to only allow expiratory gas to flow in the lower section of the circular channel 105 out through the vent 107. Similarly, the one-way gas valve 129 may be configured to only allow inspiratory gas to flow from the vent 107 through the top portion of the circular channel 105. The vent 107 may or may not allow a portion of the expiratory gas to mix with the inspiratory gas.

Embedded within the acoustic flow channel 121 may be an acoustic reflectometer 141. The acoustic reflectometer 141 may be configured to emit acoustic signals within the acoustic flow channel 121 which travel through the neck 103 and through all or portions of the intubation tube 111. These acoustic signals may also travel beyond the other end of the intubation tube 111 and into a cavity into which this end protrudes. The acoustic reflectometer 141 may be configured to detect reflections of this acoustic signal from any discontinuity within the intubation tube 111 and/or from what lies beyond.

The acoustic reflectometer 141 may be of any type. For example, the acoustic reflectometer 141 may include one or more microphones, such as a microphone 143 and 145. The acoustic reflectometer may include one or more loud speakers, such as a loud speaker 147. The components of the acoustic reflectometer 141 may be mounted so that they are flush with the inner surface of the acoustic flow channel 121, so as to not cause any acoustic discontinuity. The acoustic flow channel 121 may be straight, curved, coiled, or have a serpentine shape. The gas flow channel 123 may have a complementary configuration.

The acoustic reflectometer 141 and/or one or more of its components may be configured to be detachable from the acoustic flow channel 121, so that different acoustic reflectometers and/or different acoustic reflectometer components can be used for different applications, for cleaning, and/or as replacements.

A heater (not shown) may be provided to warm one or more of the components of the acoustic reflectometer 141. Any temperature may be used. For example, the heater may be configured to warm these components to a temperature that is above the temperature of expiratory gas from the patient.

One or more of the components of the acoustic reflectometer, such as one or more of the microphones and/or loud speakers, may be coated with a hydrophobic substance to protect these components from moisture.

The various channels which have been described may have any cross-sectional shape and may be made of any material. For example, one or more of the channels may have a circular cross-section and may be made of tubing, such as plastic tubing.

The acoustic flow channel 121, the neck 103, and the intubation tube may all have a circular cross-section. In one embodiment, the diameter of the circular cross-section of the acoustic flow channel 121, the neck 103, and the intubation tube 111 may be substantially the same. The acoustic flow channel 121, the neck 103, and the intubation tube 111 may also share a common central axis. The length of the acoustic flow channel 121 may vary and may be based upon signal processing needs, the number of microphones that are used, and/or any other criteria.

The acoustic reflectometer 141 may include appropriate electronics to generate the needed acoustic signals and to process the reflections which are detected by one or more of its microphones. The electronics may be located near the microphones 143 and 145, near the loud speaker 147, may be separated from them both, or may be partially located near one or more of these components and partially located elsewhere. The electronics may be positioned so as to not interfere with the acoustics within the acoustic flow channel 121.

One or more gas valves may be provided within the valve and channel arrangement 101, such as a gas valve 151 at a front end of the acoustic flow channel 121 and a gas valve 153 at a rear end of the acoustic flow channel 121.

FIG. 1(a) illustrates the gas valves 151 and 153 in a closed position. While in this position, expiratory gas may flow from an end of the intubation tube 111 through the detachable coupling 113, through the neck 103, through the gas flow channel 123, through the lower portion of the circular channel 105, through the one-way gas valve 127, and out through the vent 107. Such expiratory gas may not be able to flow through the acoustic flow channel 121 due to the closure of the gas valves 151 and 153, nor may it be able to flow through the upper portion of the circular channel 105 due to the closure of the one-way gas valve 129. While in this closed position, the gas valves 151 and 153 may protect the components of the acoustic reflectometer 141 from the potentially-adverse effects of the expiratory gas from the intubation tube 111, such as humidity, temperature, and/or pressure.

FIG. 1(b) illustrates the gas valves 151 and 153 in an open position. While in this position, gas may not be able to flow through the gas flow channel 123. Instead, gas may only be able to flow through the acoustic flow channel 121. More specifically, inspiratory gas may flow into the vent 107, through the one-way gas valve 129, through the top portion of the circular channel 105, through the acoustic flow channel 121, through the neck 103, through the detachable coupling 113, and into the end of the intubation tube 111. Since this gas may be dry, the acoustic reflectometer 141 may still be protected against the adverse effects of expiratory gas, such as humidity, temperature, and/or pressure.

The gas valves 151 and 153 may be operated so as to be closed when expiratory gas is flowing from the end of the intubation tube 111. When so operated, the acoustic reflectometer 141 may be protected against potentially-adverse effects of such expiratory gas, such as humidity, temperature, and/or pressure.

The gas valves 151 and 153 may be operated so as to be open only during one or more pauses between the inspiratory and expiratory gas flow. When so operated, the acoustic reflectometer 141 may be protected against potentially-adverse effects that might be caused by contaminants or other potential problems with the inspiratory gas from the vent 107. Such brief openings of the gas valves 151 and 153 may enable humidity, temperature, and/or pressure which may have built-up within the acoustic gas flow channel 121 to dissipate.

While the gas valves 151 and 153 are open, the acoustic reflectometer 141 may be operated so as to take one or more acoustic readings of any or all portions of the lumen within the intubation tube 111 and/or the cavity beyond it.

The gas valves 151 and 153 may be of any type. For example, they may be configured to operate under mechanical, electrical, pneumatic, and/or any other type of control.

A gas valve controller 161 may be provided to control the operation of the gas valves, such as the gas valves 151 and 153. The gas valve controller 161 may be configured to cause the gas valves 151 and 153 to open only during periods of inspiratory gas flow from the intubation tube 111 or only during pauses between successive ventilator breaths. One complete ventilator breath may consist of a) an inspiratory breath generated by positive pressure; and (b) an expiratory unforced breath that is due to passive exhalation of the gas by the patient. The gas valve controller 161 may be configured to cause the gas valves 151 and 153 to open during a pause between successive inspiratory-expiratory ventilator breaths. The gas valve controller 161 may be configured to control the gas valves 151 and 153 through means which are appropriate for the gas valves, such as through electrical signals when the gas valves are configured to be electrically controlled, through mechanical forces when the gas valves are configured to be mechanically controlled, through pneumatic pressure when the gas valves are configured to be pneumatically controlled, and/or through other means when the gas valves are configured to be controlled by other means.

One or more gas flow sensors may be provided to provide the gas valve controller 161 with information about the state of the gas flow within the intubation tube 111 so as to enable the gas valve controller 161 to signal the gas valves 151 and 153 to open and close at desired times, such as at one or more of the times discussed above. Such gas flow sensors may be of any type. For example, they may include one or more pressure sensors and/or $CO_2$ sensors.

These sensors may be positioned anywhere within the gas flow which is appropriate for sensing the gas flow. In one embodiment, for example, a gas flow sensor may be embedded in the vicinity of the one-way gas valve 127 and/or in the vicinity of the one-way gas valve 129 or in the vicinity of the adapter 113. Each of these sensors may be configured to detect when their respective one-way gas valve is open and/or closed. Based on the signals from these sensors, the gas valve controller 161 may be configured to determine when there is inspiratory gas flow, expiratory gas flow, and/or no gas flow. The gas valve controller 161 may be configured to control the gas valves 151 and 153 in accordance with these determinations, such as to close these gas valves during expiratory gas flow or only during one or more pauses between gas flow.

The humidifier 109 may be configured to add humidity into gas flowing through the gas flow channel 123. The humidifier 109 may instead be located at any other point along the gas flow. For example, the humidifier 109 may be located within the lower portion of the circular channel, in which case the vent 107 may be configured to re-circulate a portion of the expiratory gas during the inspiratory flow. When placed in line with gas which flows though the acoustic gas flow channel 121, the humidifier may be turned off when the valves 151 and 153 are open, so as to avoid injecting humidity into the acoustic gas flow channel 121. The humidifier 109 may be configured to be detached for cleaning, replacement, or when not needed.

Figure 2A:
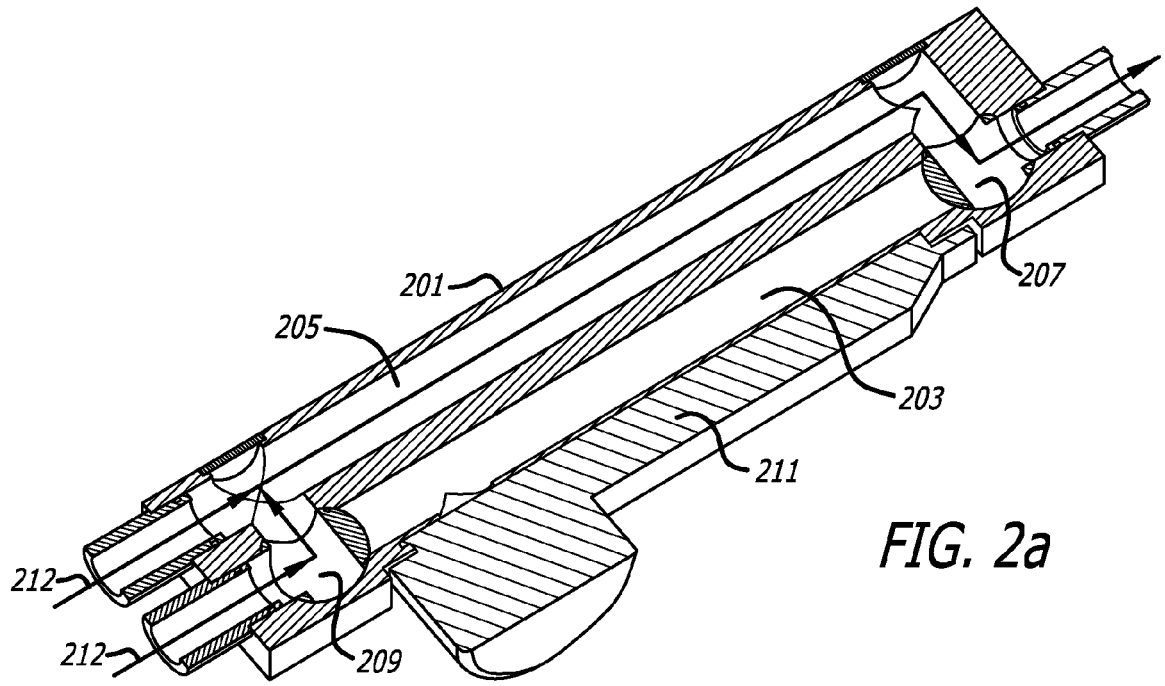
FIG. 2(a) illustrates a valve and channel arrangement that may be used in the instrument illustrated in FIGS. 1(a) and 1(b). The arrangement is illustrated in an inactive position.
Figure 2B:
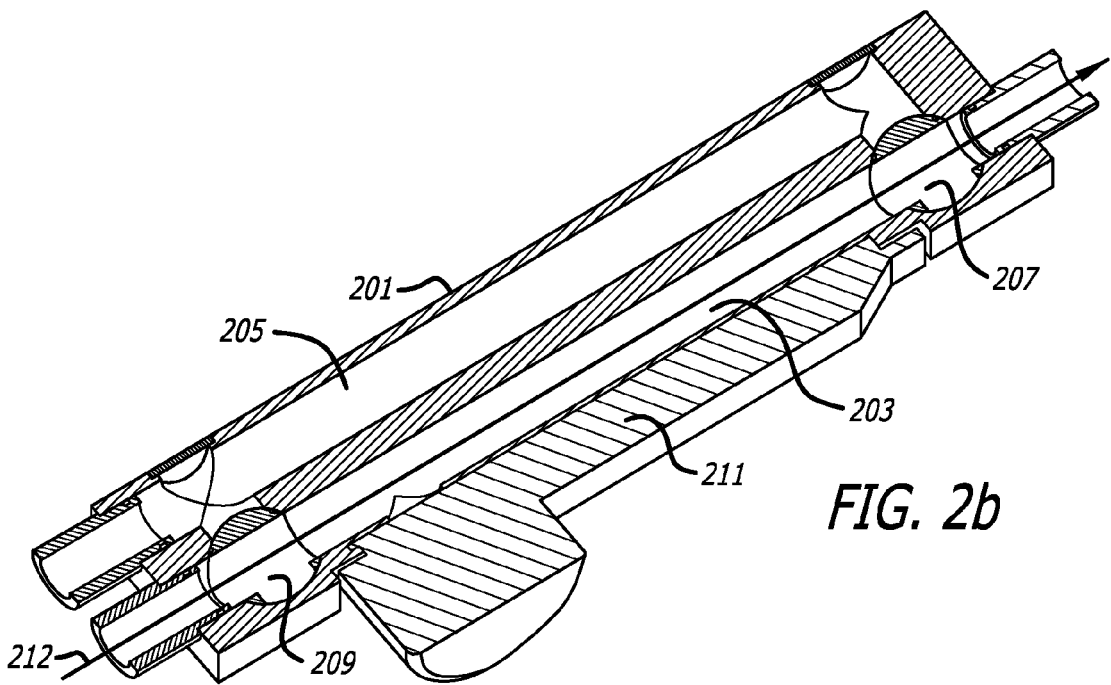
FIG. 2(b) illustrates the valve and channel arrangement in FIG. 2(a) in an active position.
Figure 3A:
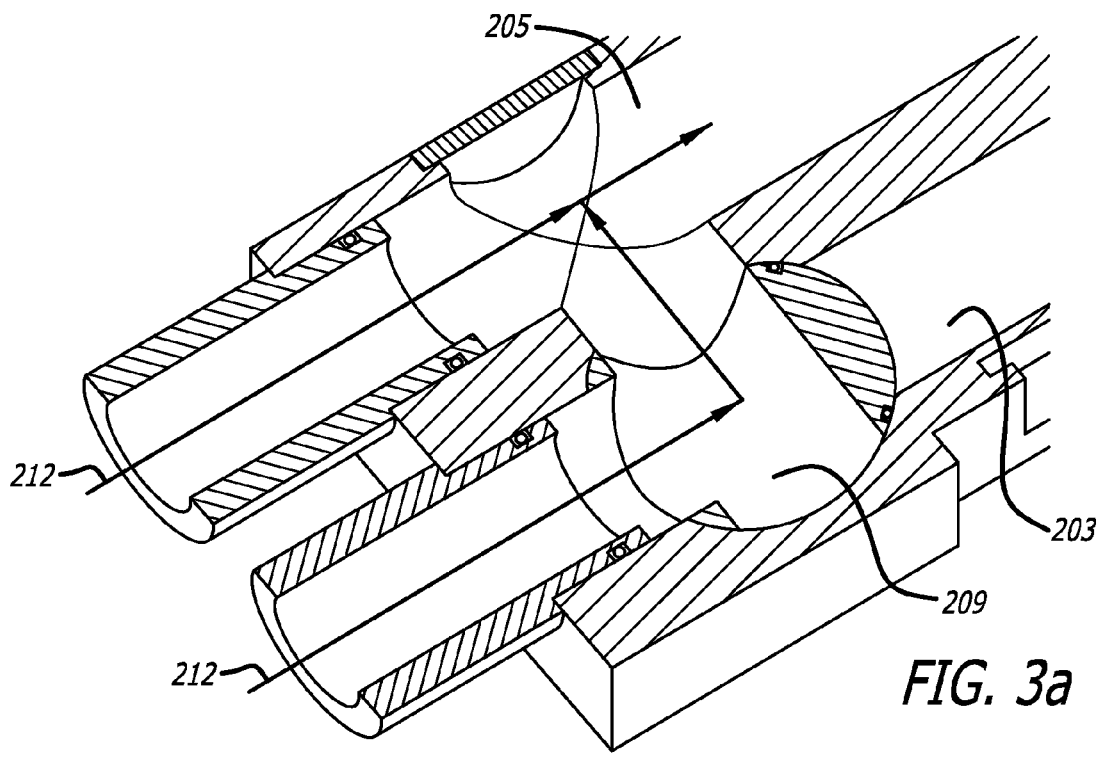
FIG. 3(a) illustrates an enlarged view of one of the valves illustrated in FIGS. 2(a) and 2(b) in an inactive position.
Figure 3B:
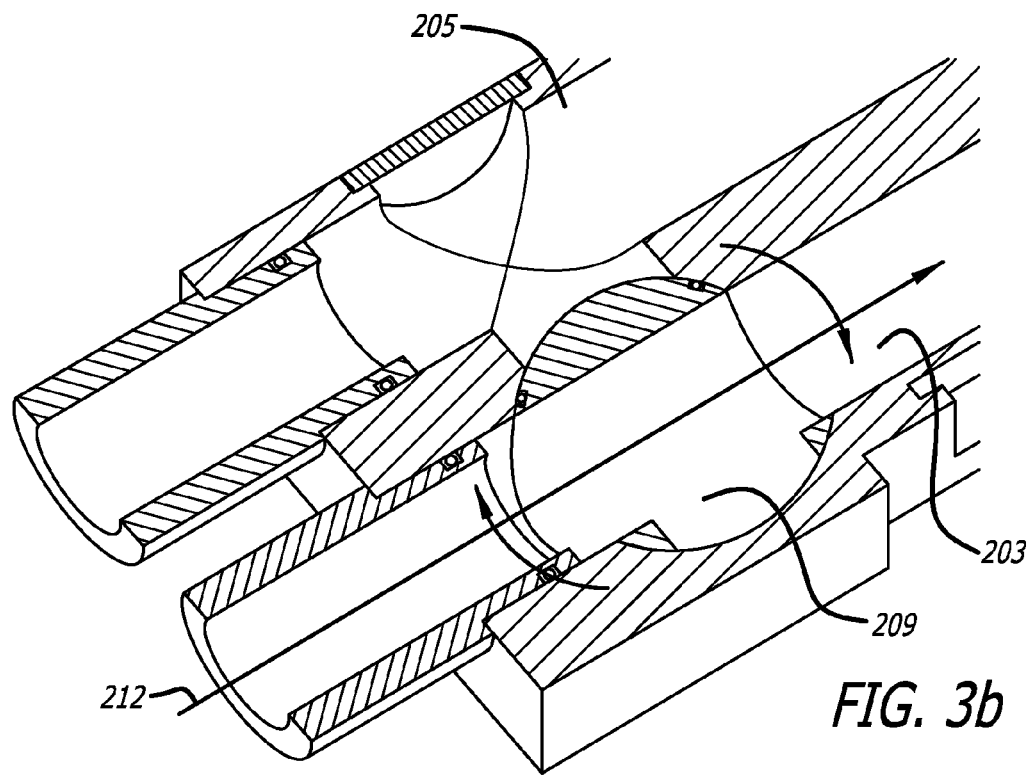
FIG. 3(b) illustrates the enlarged view of the valve in FIG. 3(a) in an active position.

FIG. 2(a) illustrates a valve and channel arrangement that may be used in the instrument illustrated in FIGS. 1(a) and 1(b) in an inactive position. FIG. 3(a) illustrates an enlarged view of one of the valves illustrated in FIG. 2(a) in an inactive position. FIG. 2(b) illustrates the valve and channel arrangement in FIG. 2(a) with the valves in an active position. FIG. 3(b) illustrates the enlarged view of the valve in FIG. 3(a) in an active position. A valve and channel arrangement may be used for the valve and channel arrangement 101 in FIGS. 1(a) and 1(b) that is different from what is illustrated in FIGS. 2(a), 2(b), 3(a), and 3(b). Similarly, the valve and channel arrangement that is illustrated in FIGS. 2(a), 2(b), 3(a), and 3(b) may be used in an instrument other than the one illustrated in FIGS. 1(a) and 1(b).

As illustrated in FIGS. 2(a) and 2(b), the valve and channel arrangement may include an elongated structure 201 which may include an acoustic flow channel 203 and a gas flow channel 205. The elongated structure 201 may also include one or more internal gas valves, such as a gas valve 207 at one end of the acoustic flow channel 203 and a gas valve 209 at another end of the acoustic flow channel 203. An acoustic reflectometer 211 may be detachably attached to the elongated structure 201.

The acoustic flow channel 203, the gas flow channel 205, the gas valves 207 and 209, and the acoustic reflectometer 211 may correspond, respectively, to the acoustic flow channel 121, the gas flow channel 123, the gas valves 151 and 153, and the acoustic reflectometer 141 that are illustrated in FIGS. 1(a) and 1(b) and discussed above. They may have any of the compositions, configurations, and functions as also described above in connection with their corresponding component.

The gas valves 207 and 209 may be configured to rotate approximately 90 degrees between their fully closed position, illustrated in FIGS. 2(a) and 3(a), and their fully open position, illustrated in FIGS. 2(b) and 3(b). As illustrated in FIGS. 2(b) and 3(b)., moreover, the gas valves 207 and 209 may be configured so as to provide a smooth continuous acoustical path so as not to cause any disruption in the acoustical pathway between the acoustic flow channel 203 and the channels which connect to it while in their open position.

As illustrated in FIGS. 2(a) and 3(a), all inspiratory gas flow 212 may be channeled through the gas flow channel 205, while no portion of the inspiratory gas flow 212 may travel through the acoustic flow channel 203, while the gas valves 207 and 209 are in their closed position. Conversely, all of the inspiratory gas flow 212 may flow through the acoustic flow channel 203, while no portion of it may flow through the gas flow channel 205, while the gas valves 207 and 209 are in their open position, as illustrated in 2(b) and 3(b). In other configurations, the gas valves 207 and 209 may only be opened during pauses between gas flow, as discussed above in connection with FIGS. 1(a) and 1(b), in which case the inspiratory gas flow would never flow though the acoustic flow channel 203.

Figure 4A:
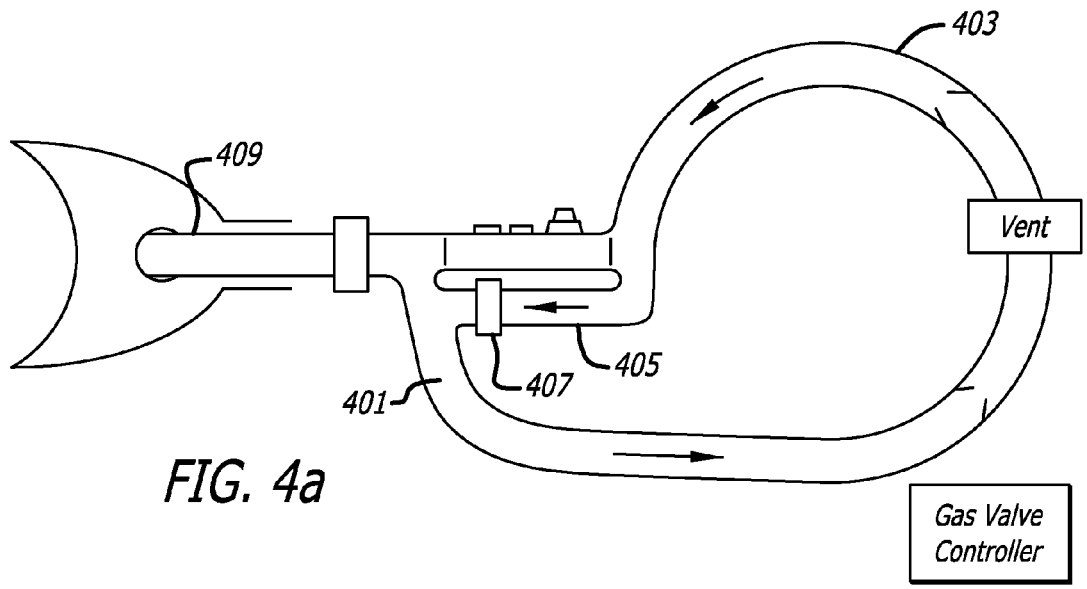
FIG. 4(a) illustrates another embodiment of an instrument for continuously monitoring acoustic reflections from within and/or beyond an intubation tube positioned within the mouth of a patient while the patient is breathing. The instrument is in an inactive state.
Figure 4B:
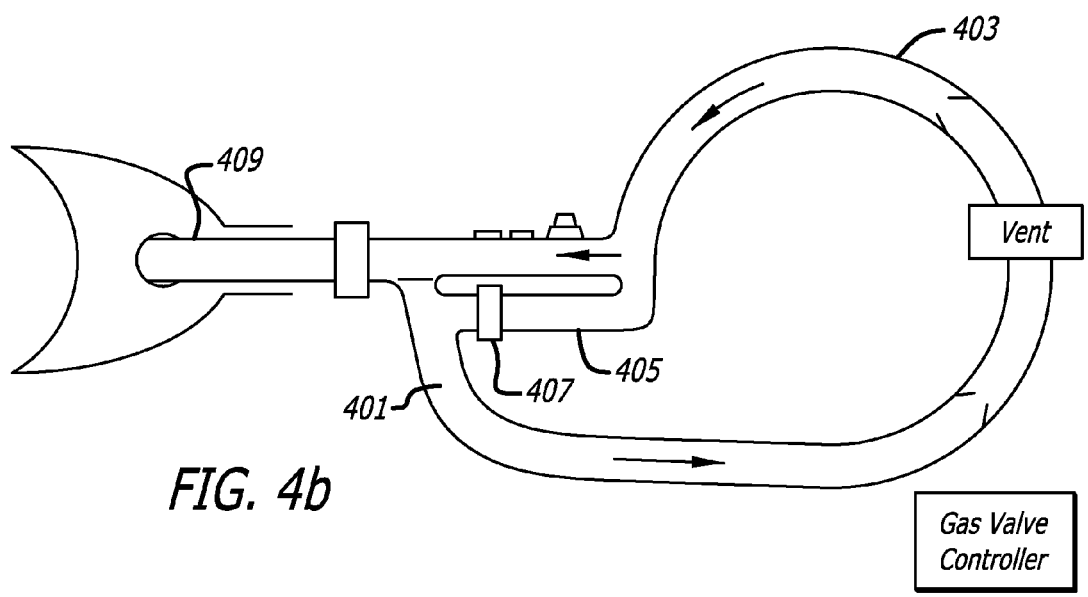
FIG. 4(b) illustrates the instrument in FIG. 4(a) in an active state.

FIG. 4(a) illustrates another embodiment of an instrument for continuously monitoring acoustic reflections from within and/or beyond an intubation tube positioned within the mouth of a patient while the patient is breathing. The instrument is in an inactive state. FIG. 4(b) illustrates the instrument in FIG. 4(a) in an active state.

The instrument illustrated in FIGS. 4(a) and 4(b) is comparable to the instrument illustrated in FIGS. 1(a) and 1(b) and described above in connection with these figures. A duplicative discussion of its components therefore, will not be provided. Instead, reference is made above to the discussion of their comparable components, which may be equally applicable.

One notable difference may be that an input 401 to a lower portion of a circular channel 403 is connected at the left side of a gas flow channel 405, rather than to the right side of the gas flow channel 123 as is illustrated in FIGS. 1(a) and 1(b). This difference in connectivity may prevent expiratory gas from flowing through the gas flow channel 405, unlike the expiratory gas that may flow through the gas flow channel 123 illustrated in FIG. 1(a).

Figure 5:
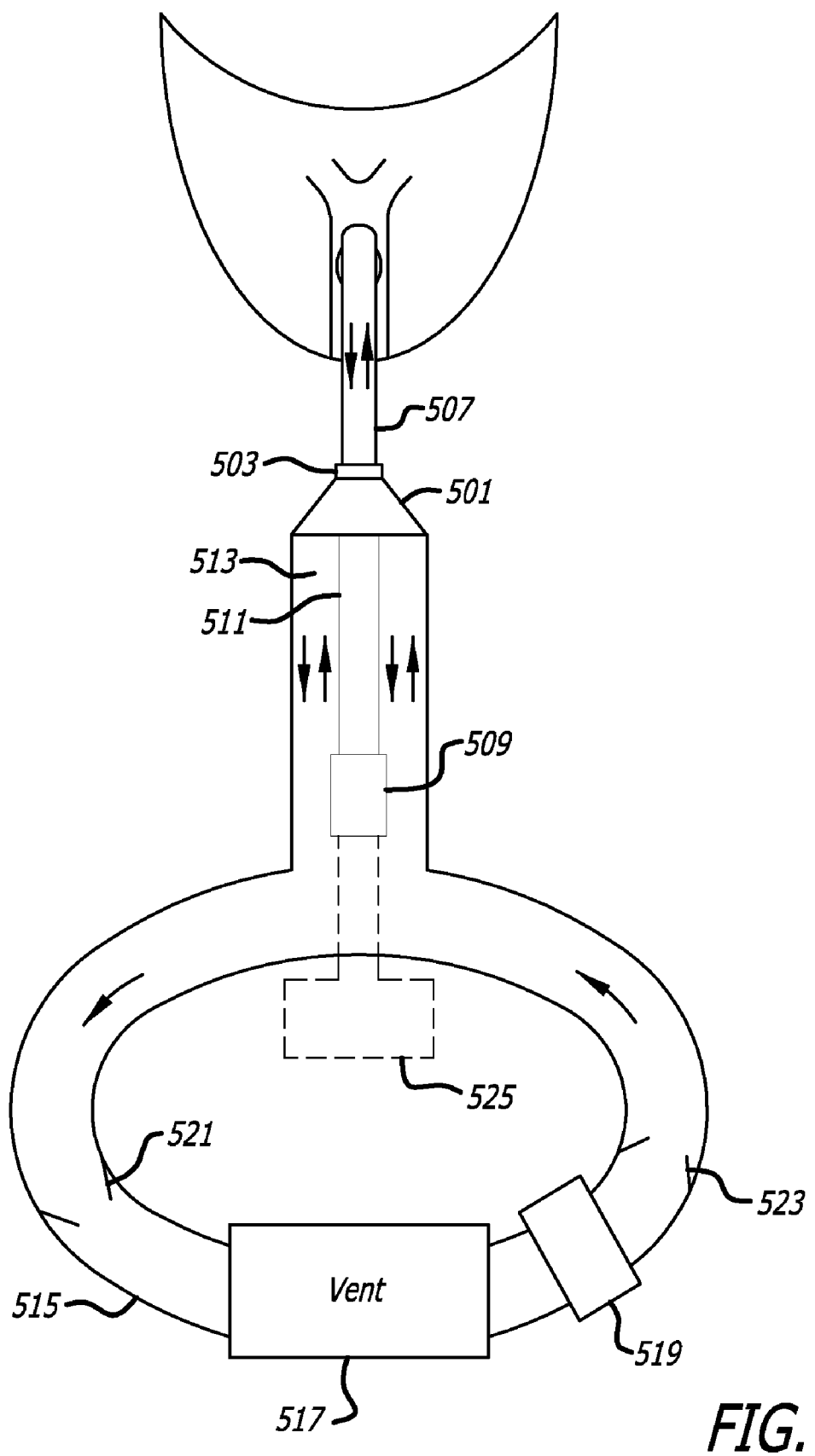
FIG. 5 illustrates another embodiment of an instrument for continuously monitoring acoustic reflections from within and/or beyond an intubation tube positioned within the mouth of a patient while the patient is breathing.

FIG. 5 illustrates another embodiment of an instrument for continuously monitoring acoustic reflections from within and/or beyond an intubation tube positioned within the mouth of a patient while the patient is breathing. The instrument illustrated in FIG. 5 has similarities to the instrument illustrated in FIGS. 1(a) and 1(b), as well as differences.

As illustrated in FIG. 5, the instrument may include a neck 501 and a detachable coupling 503 configured to detachably couple the neck 501 to an intubation tube 507. An acoustic reflectometer 509 may be mounted within an acoustic flow channel 511 which may be surrounded by a gas flow channel 513. A circular channel 515 may include a vent 517, a humidifier 519, a one-way gas valve 521, and a one-way gas valve 523.

Each of the components of FIG. 5 which have now been identified may be configured and may function in the same way as their corresponding components in FIGS. 1(a) and 1(b), as discussed above, with possible differences.

One difference may be that there may be no gas valves within the acoustic flow channel 511. Instead, gas may be prevented from flowing through the acoustic flow channel 511 by virtue of it being blocked at an end of the acoustic flow channel 511 furthest from the intubation tube 507. Instead, inspiratory and expiratory gas may flow around the perimeter of the acoustic flow channel 511 through the gas flow channel 513. In one embodiment, inspiratory cold dry gas may be injected into the acoustic flow channel 511 at various times in order to clear any expiratory gas which may have migrated within the acoustic flow channel 511. In a still further embodiment, the acoustic reflectometer 509 may be mounted outside of the acoustic flow channel 511, such as is illustrated by the dashed box 525.

Figure 6:
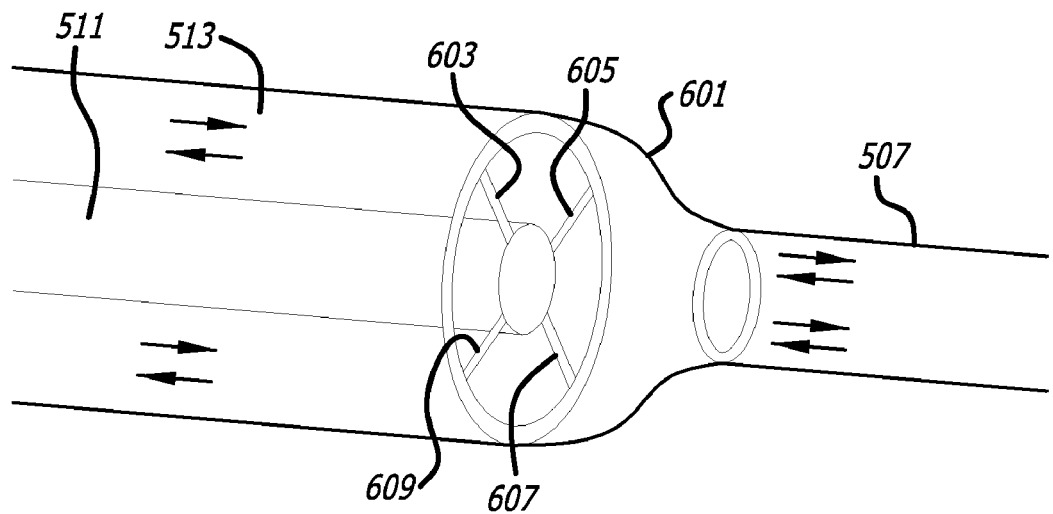
FIG. 6 illustrates one embodiment of a neck portion that may be used in connection with the instrument illustrated in FIG. 5.

FIG. 6 illustrates one embodiment of a neck portion that may be used in connection with the instrument illustrated in FIG. 5. As illustrated in FIG. 6, the intubation tube 507 may be connected to the gas flow channel 513 by a tapered neck 601. The tapered neck 601 may include one or more anchoring spokes, such as anchoring spokes 603, 605, 607, and 609, to position the acoustic flow channel 511 such that its central access is co-aligned with the central access of the intubation tube 507. The cross-section of the acoustic flow channel 511 and the intubation tube 507 may also both be substantially cylindrical and of substantially the same diameter.

Figure 7:
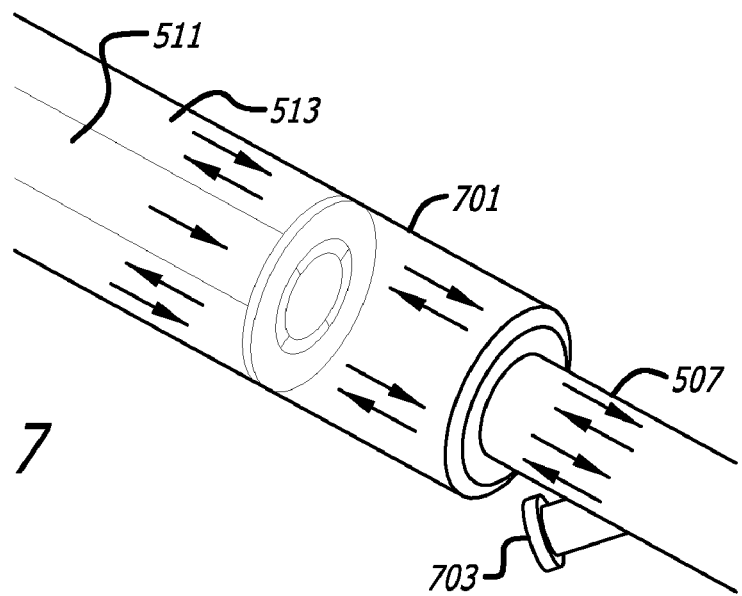
FIG. 7 illustrates another embodiment of a neck portion that may be used in connection with the instrument illustrated in FIG. 5.

FIG. 7 illustrates another embodiment of a neck portion that may be used in connection with the instrument illustrated in FIG. 5. The embodiment illustrated in FIG. 7 is comparable to the embodiment illustrated in FIG. 6, except that a neck 701 may not have any taper at all.

A suction port 703 may be provided to facilitate the insertion of a suction catheter (not shown). A suction catheter may be inserted within the suction port 703 and used to remove any buildup which may occur within the intubation tube 507, such as a mucus buildup, or beyond the intubation tube. The suction port may be located elsewhere, such as in the acoustic flow channel 511. A comparable suction port may be provided in the other embodiments of instruments described herein.

The components, steps, features, objects, benefits and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits and advantages. These also include embodiments in which the components and/or steps are arranged and/or ordered differently.

For example, the instrument may be configured in a closed circular system, as well as in a coaxial Bain circuit system or in other Mapleson type non-rebreathing systems. A mechanical ventilator may be added to pump inspiratory gas into the patient through the intubation tube. The embedded acoustic reflectometer may also or instead be used during spontaneous breathing.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications which have been cited in this disclosure are hereby incorporated herein by reference.

The phrase "means for" when used in a claim is intended to and should be interpreted to embrace the corresponding structures and materials that have been described and their equivalents. Similarly, the phrase "step for" when used in a claim embraces the corresponding acts that have been described and their equivalents. The absence of these phrases means that the claim is not intended to and should not be interpreted to be limited to any of the corresponding structures, materials, or acts or to their equivalents.

Nothing that has been stated or illustrated is intended or should be interpreted to cause a dedication of any component, step, feature, object, benefit, advantage, or equivalent to the public, regardless of whether it is recited in the claims.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

The invention claimed is:

1. An instrument for continuously monitoring acoustic reflections from within and/or beyond an intubation tube positioned within the mouth of a patient while the patient is breathing comprising:
   an acoustic reflectometer configured to detect the acoustic reflections;
   an acoustic flow channel containing the acoustic reflectometer within it, the acoustic flow channel being configured to acoustically couple the acoustic reflectometer to an end of the intubation tube, but to substantially block the free flow of expiratory gas from the end of the intubation tube through the acoustic flow channel, wherein the end of the intubation tube and the acoustic flow channel share a central axis;
   a gas flow channel that is separate from the acoustic flow channel and that is configured to allow the free flow of expiratory gas from the end of the intubation tube through the gas flow channel;
   a gas valve configured to:
      block expiratory gas from flowing from the end of the intubation tube into the acoustic flow channel when in a closed position; and
      not cause a substantial disruption in acoustic energy traveling from the acoustic reflectometer within the acoustic gas channel into the end of the intubation tube when in an open position;
   a gas flow sensor configured to sense the flow of gas through the end of the intubation tube; and
   a gas valve controller configured to control the gas valve and to cause the gas valve to be in the closed position when the gas flow sensor detects the flow of expiratory gas from the end of the intubation tube.

2. The instrument of claim 1 wherein the end of the intubation tube and the acoustic flow channel each have a substantially cylindrical cross-section of approximately the same diameter.

3. The instrument of claim 1 wherein the gas valve is located at an end of the acoustic flow channel which is closest to the end of the intubation tube and further comprising a second gas valve located at the other end of the acoustic flow channel.

4. The instrument of claim 1 wherein the gas valve controller is configured to cause the gas valve to:
   be in the closed position when the gas flow sensor detects the flow of inspiratory gas through the end of the intubation tube; and
   momentarily move to the open position between the end of the flow of expiratory gas from the end of the intubation tube and the beginning of the flow of inspiratory gas into the end of the intubation tube.

5. The instrument of claim 1 further comprising a second gas flow channel that is separate from the acoustic flow channel and the other gas flow channel and that is configured to allow the free flow of inspiratory gas through the second gas flow channel and into the end of the intubation tube.

6. The instrument of claim 5 further comprising a gas valve configured:
   when in a closed position to:
      block expiratory gas from flowing from the end of the intubation tube into the acoustic flow channel; and
      allow the free flow of inspiratory gas from the gas flow channel into the end of the intubation tube; and
   when in an open position to:
      allow the free flow of inspiratory gas to flow through the acoustic flow channel into the end of the intubation tube; and
      block inspiratory gas from flowing though the gas flow channel into the end of the intubation tube.

7. The instrument of claim 5 wherein the gas flow channel includes a humidifier configured to humidify gas which passes through the inspiratory gas flow channel.

8. The instrument of claim 1 wherein the acoustic reflectometer includes components and further comprising a heater configured to heat one or more of the components.

9. The instrument of claim 1 wherein the acoustic reflectometer includes components and further comprising a hydrophobic substance covering one or more of the components.

10. The instrument of claim 1 further comprising a coupling configured to detachably couple the instrument to the end of the intubation tube.

11. The instrument of claim 1 further comprising the intubation tube.

12. The instrument of claim 11 wherein the intubation tube is an endotracheal tube.

13. The instrument of claim 11 wherein the intubation tube is a laryngeal mask airway tube.

14. The instrument of claim 1 wherein the acoustic flow channel and the gas flow channel may parallel one another within a single tube.

15. The instrument of claim 14 wherein the central axis of the single tube is substantially co-aligned with the central axis of the acoustic flow channel and the central axis of the gas flow channel.

* * * * *